(12) United States Patent
Neumann

(10) Patent No.: US 11,145,401 B1
(45) Date of Patent: Oct. 12, 2021

(54) SYSTEMS AND METHODS FOR GENERATING A SUSTENANCE PLAN FOR MANAGING GENETIC DISORDERS

(71) Applicant: KPN INNOVATIONS, LLC., Lakewood, CO (US)

(72) Inventor: Kenneth Neumann, Lakewood, CO (US)

(73) Assignee: KPN INNOVATIONS, LLC., Lakewood, CO (US)

( * ) Notice: Subject to any disclaimer, the term of this patent is extended or adjusted under 35 U.S.C. 154(b) by 0 days.

(21) Appl. No.: 17/136,151

(22) Filed: Dec. 29, 2020

(51) Int. Cl.
*G16H 50/20* (2018.01)
*G16H 20/60* (2018.01)
*G06N 20/00* (2019.01)
*G16H 10/60* (2018.01)
*G16H 50/30* (2018.01)

(52) U.S. Cl.
CPC ............ *G16H 20/60* (2018.01); *G06N 20/00* (2019.01); *G16H 10/60* (2018.01); *G16H 50/30* (2018.01)

(58) Field of Classification Search
CPC ........ G06Q 50/00; G06Q 50/22; G06F 15/18; G06F 19/24; G16H 50/20
USPC .......................................... 705/2, 3; 706/12
See application file for complete search history.

(56) References Cited

U.S. PATENT DOCUMENTS

| | | | | |
|---|---|---|---|---|
| 7,444,308 B2* | 10/2008 | Guyon | ................... | G16B 40/00 706/12 |
| 10,446,272 B2* | 10/2019 | Wilde | ................... | G16B 40/00 |
| 2007/0196841 A1 | 8/2007 | Ruano | | |
| 2008/0221932 A1 | 9/2008 | Kane | | |
| 2008/0275912 A1 | 11/2008 | Roberts | | |
| 2008/0317733 A1 | 12/2008 | Azimi | | |
| 2010/0042438 A1* | 2/2010 | Moore | ................... | G16B 20/00 705/3 |
| 2010/0070455 A1 | 3/2010 | Halperin | | |
| 2010/0105038 A1 | 4/2010 | Draper | | |
| 2010/0153016 A1 | 6/2010 | Stefanon | | |

(Continued)

FOREIGN PATENT DOCUMENTS

| | | |
|---|---|---|
| CH | 713713 A2 | 10/2018 |
| CH | 713714 A2 | 10/2018 |

(Continued)

OTHER PUBLICATIONS

Google patents search, Dec. 18, 2021 (Year: 2021).*

(Continued)

*Primary Examiner* — Dilek B Cobanoglu
(74) *Attorney, Agent, or Firm* — Caldwell Intellectual Property Law, LLC

(57) ABSTRACT

A system for generating a sustenance plan for managing genetic disorders is disclosed. The system includes a computing device. The computing device is configured to receive an input which may include genetics test data. The computing device is configured to identify a plurality of biological indices of a disease state as a function of the genetics test data. The plurality of biological indices comprises at least one biological index related to a genetic disease state. The computing device is configured to generate a genetic disorder classifier. The computing device is configured to generate a sustenance plan as a function of the positive result. A method for generating a sustenance plan for managing genetic disorders is disclosed.

18 Claims, 6 Drawing Sheets

(56) References Cited

U.S. PATENT DOCUMENTS

| | | |
|---|---|---|
| 2011/0159489 A1 | 6/2011 | Sancak |
| 2012/0277180 A1 | 11/2012 | Marini |
| 2013/0151270 A1* | 6/2013 | Nova .................... G16H 10/60 |
| | | 705/2 |
| 2016/0140288 A1 | 5/2016 | Kuan |
| 2017/0268057 A1 | 9/2017 | Tranah |
| 2019/0080051 A1* | 3/2019 | Menche ................. G16B 20/00 |

FOREIGN PATENT DOCUMENTS

| | | |
|---|---|---|
| CN | 104651485 A | 5/2015 |
| RU | 2691145 C2 | 6/2019 |
| WO | 2019074388 A1 | 4/2019 |

OTHER PUBLICATIONS ip.com search, Jun. 7, 2021 (Year: 2021).*

Title: Improved weight management using genetic information to personalize a calorie controlled diet; by: Arkadiano; Date:Oct. 18, 2017.

Title: The PNPLA3 1148M variant and chronic liver disease: When a genetic mutation meets nutrients; by: Maglio; Date: Oct. 11, 2013.

* cited by examiner

SYSTEMS AND METHODS FOR GENERATING A SUSTENANCE PLAN FOR MANAGING GENETIC DISORDERS

FIELD OF THE INVENTION

The present disclosure generally relates to the field of nutrition for disease management. In particular, the present invention is directed to a system and method for a sustenance plan for managing genetic disorders.

BACKGROUND

Nutrition is an essential function of life as it provides the necessary nutrients the body needs to sustain all functions of life. The use of artificial intelligence in the field of nutrition may assist in the development and management of a healthy lifestyle for an individual.

SUMMARY OF THE DISCLOSURE

In an aspect of the disclosure, a system for generating a sustenance plan for managing genetic disorders is disclosed. The system includes a computing device. The computing device is configured to receive an input which may include genetic test data. The computing device is configured to identify a plurality of biological indices of a disease state as a function of the genetic test data. The plurality of biological indices comprises at least one biological index related to a genetic disease state. The computing device is configured to generate a genetic disorder classifier. Generating the genetic disorder classifier includes receiving genetic disorder training data correlating biological indices of genetic disorders and genetic markers to genetic disorder labels. Generating the genetic disorder classifier includes training, using the genetic disorder classifier, the at least one biological index and at least one genetic marker to a positive result for a genetic disorder. The computing device is configured to generate a sustenance plan as a function of the positive result.

In another aspect of the disclosure, a method for generating a sustenance plan for managing genetic disorders is disclosed. The method receives an input which may include genetic test data. The method identifies a plurality of biological indices of a genetic disease state as a function of the genetic test data. The plurality of biological indices comprises at least one biological index related to a genetic disease state. The method generates a genetic disorder classifier. Generating the genetic disorder classifier includes receiving genetic disorder training data correlating biological indices of genetic disorders and genetic markers to genetic disorder labels. Generating the genetic disorder classifier includes training, using the genetic disorder classifier, the at least one biological index and at least one genetic marker to a positive result for a genetic disorder. The method generates a sustenance plan as a function of the positive result.

These and other aspects and features of non-limiting embodiments of the present invention will become apparent to those skilled in the art upon review of the following description of specific non-limiting embodiments of the invention in conjunction with the accompanying drawings.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein.

The drawings are not necessarily to scale and may be illustrated by phantom lines, diagrammatic representations and fragmentary views. In certain instances, details that are not necessary for an understanding of the embodiments or that render other details difficult to perceive may have been omitted.

DETAILED DESCRIPTION

At a high level, aspects of the present disclosure are directed to systems and methods for generating a sustenance plan for managing genetic disorders. The system may include a computing device that may receive an input which may be in the form of a biochemical generic test. The input may include genetic test data which may be used in identifying biological indices related to a genetic disorder. A classifier is trained and used to classify at least one biological index of a genetic disorder and genetic markers to a positive result indicating the presence of a genetic disorder. A positive result may generate an alimentary plan to treat and/or prevent the genetic disorder.

A practical application of this technology includes the use of a machine-learning model to provide a user access to alimentary plans that may improve a genetic disorder. The system and method may analyze the progression of the genetic disorder as measured by the presence or absence of the biological index. The machine-learning model may also be train to output other disease states that may be related to the genetic disorder. The system and method allow for an update of the alimentary plan if the genetic disorder continues to progress.

Figure 1:
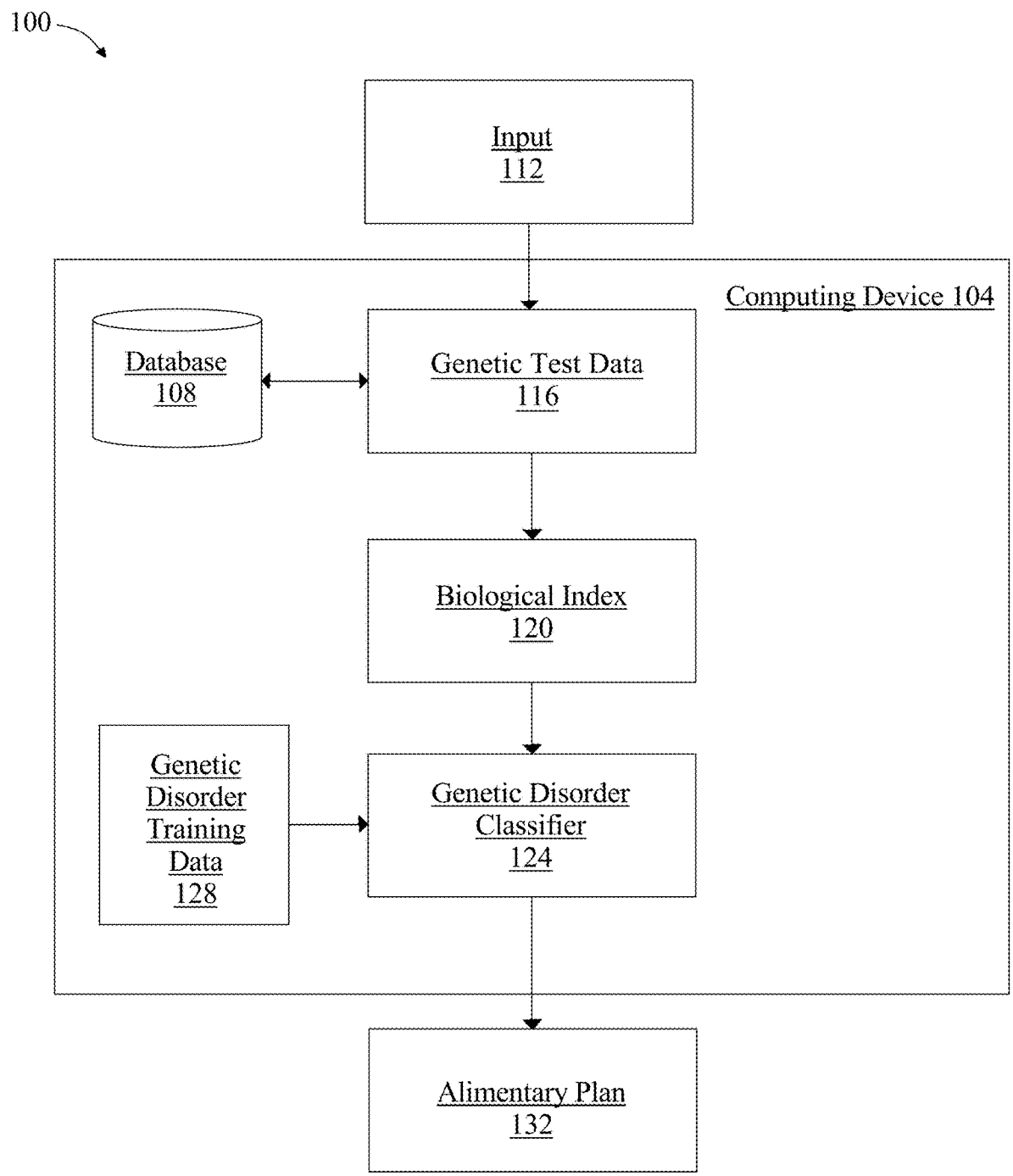
FIG. 1 is a block diagram of an exemplary embodiment of a system of determining a sustenance plan for managing a genetic disorder.

Referring now to FIG. 1, an exemplary embodiment of a system 100 for generating an alimentary plan for managing a skin disorder is illustrated. System includes a computing device 104. Computing device 104 may include any computing device as described in this disclosure, including without limitation a microcontroller, microprocessor, digital signal processor (DSP) and/or system on a chip (SoC) as described in this disclosure. Computing device 104 may include, be included in, and/or communicate with a mobile device such as a mobile telephone or smartphone. Computing device 104 may include a single computing device operating independently, or may include two or more computing device operating in concert, in parallel, sequentially or the like; two or more computing devices may be included together in a single computing device or in two or more computing devices. Computing device 104 may interface or communicate with one or more additional devices as described below in further detail via a network interface device. Network interface device may be utilized for connecting a computing device to one or more of a variety of networks, and one or more devices. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network may employ a wired and/or a wireless mode of communication. In general, any network topology may be used. Information (e.g., data, software etc.) may be communicated to and/or from a computer and/or a computing device. Computing device 104 may include but is not limited to, for example, a computing device or cluster of computing devices in a first location and a second computing device or cluster of computing devices in a second location. Computing device 104 may include one or more computing devices dedicated to data storage, security, distribution of traffic for load balancing, and the like. Computing device 104 may distribute one or more computing tasks as described below across a plurality of computing devices of computing device, which may operate in parallel, in series, redundantly, or in any other manner used for distribution of tasks or memory between computing devices. Computing device 104 may be implemented using a "shared nothing" architecture in which data is cached at the worker, in an embodiment, this may enable scalability of system 100 and/or computing device.

With continued reference to FIG. 1, computing device 104 may be designed and/or configured to perform any method, method step, or sequence of method steps in any embodiment described in this disclosure, in any order and with any degree of repetition. For instance, Computing device 104 may be configured to perform a single step or sequence repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. Computing device 104 may perform any step or sequence of steps as described in this disclosure in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

Still referring to FIG. 1, computing device 104 may connect to and/or include a database 108. Database 108 may be implemented, without limitation, as a relational database 108, a key-value retrieval database 108 such as a NOSQL database 108, or any other format or structure for use as a database 108 that a person skilled in the art would recognize as suitable upon review of the entirety of this disclosure. Database 108 may alternatively or additionally be implemented using a distributed data storage protocol and/or data structure, such as a distributed hash table or the like. Database 108 may include a plurality of data entries and/or records as described above. Data entries in a database 108 may be flagged with or linked to one or more additional elements of information, which may be reflected in data entry cells and/or in linked tables such as tables related by one or more indices in a relational database 108. Persons skilled in the art, upon reviewing the entirety of this disclosure, will be aware of various ways in which data entries in a database 108 may store, retrieve, organize, and/or reflect data and/or records as used herein, as well as categories and/or populations of data consistently with this disclosure. In some embodiments, network data, or other information such as user information, transfer party information, and alimentary provider information, may be stored in and/or retrieved from database 108.

Figure 2:
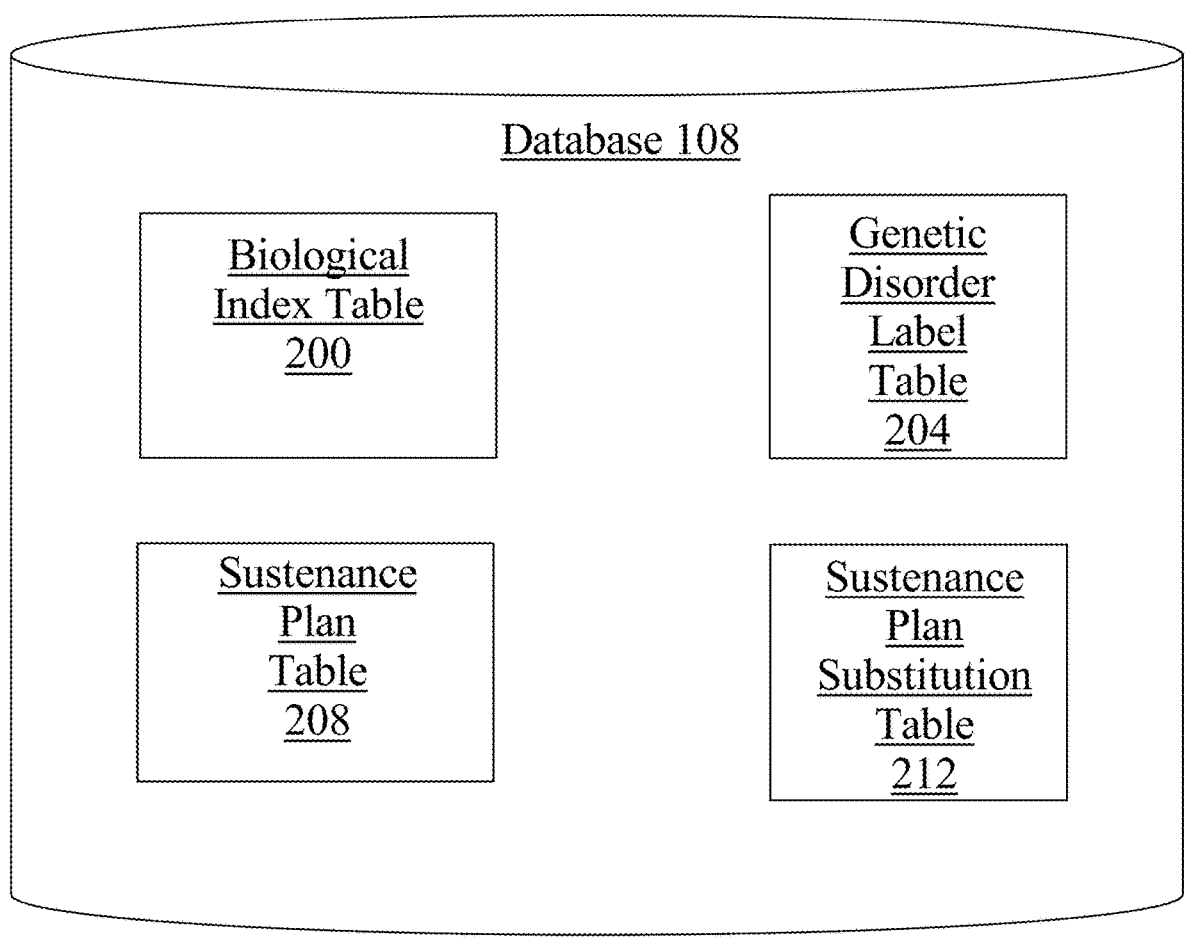
FIG. 2 is a block diagram of an exemplary embodiment of a database.

Referring now to FIG. 2 an exemplary embodiment of a database 108 is illustrated. Database 108 may, as a non-limiting example, organize data stored in the database according to one or more database tables. One or more database tables may be linked to one another by, for instance, common column values. For instance, a common column between two tables of database 108 may include an identifier of alimentary providers, for instance as defined below; as a result, a query may be able to retrieve all rows from any table pertaining to a given alimentary provider. Other columns may include any other category usable for organization or subdivision of data, including types of data, common pathways between, for example, an alimentary combination and a first alimentary provider, or the like; persons skilled in the art, upon reviewing the entirety of this disclosure, will be aware of various ways in which expert data from one or more tables may be linked and/or related to expert data in one or more other tables.

Still referring to FIG. 2, one or more database tables in database 108 may include, as a non-limiting example, a biological index table 200. Biological index table 200 may be used to store biological indices corresponding to genetic disorders, biological indices that correspond to related disease states, or the like. As another non-limiting example, one or more tables in database 108 may include a genetic disorder label table 204. Genetic disorder label table 204 may be used to store correlations between biological indices and potential genetic disorders, and the like. Another non-limiting example, one or more tables in database 108 may include a sustenance plan table 208. A sustenance plan table 208 may include, but not limited to sustenance combinations that may treat or prevent a specific genetic disorder, adverse foods affecting genetic disorders, and the like. As another non-limiting example, one or more tables in database 108 may be a sustenance plan substitution table. A sustenance plan substitution table 212 may include sustenance combinations that may include allowable substitutions for sustenance combinations, substitutions that may create an adverse effect on a genetic disorder, and the like.

Referring back to FIG. 1, computing device 104 receives input 112. Input 112 includes genetic test data 116, where genetic test data 116 includes data from a biochemical genetic test. An "input," as used in this disclosure, may include, but not limited to any medical test, a user's health assessment, a user's nutritional assessment, an assessment conducted in any website related to a genetic disorder, a direct entry from a user, and the like. As used in this disclosure, "genetic test data" is any data indicative of a person's genetic state; genetic state may be evaluated about one or more measures of health of a person's body, one or more systems within a person's body such as a circulatory system, a digestive system, a nervous system, or the like, one or more organs within a person's body, and/or any other subdivision of a person's body useful for diagnostic or prognostic purposes. For instance, and without limitation, a particular set of biomarkers, test results, and/or biochemical information may be recognized in a given medical field as useful for identifying various disease conditions or prognoses within a relevant field. For instance, and without limitation, genetics test data 116 may include genomic data, including deoxyribonucleic acid (DNA) samples and/or sequences, such as without limitation DNA sequences contained in one or more chromosomes in human cells. Genomic data may include, without limitation, ribonucleic acid (RNA) samples and/or sequences, such as samples and/or sequences of messenger RNA (mRNA) or the like taken from human cells. Genetic data may include telomere lengths. Genomic data may include epigenetic data including data describing one or more states of methylation of genetic material. Genetics test data 116 may include proteomic data, which as used herein is data describing all proteins produced and/or modified by an organism, colony of organisms, or system of organisms, and/or a subset thereof. Genetics test data may include data concerning a microbiome of a person, which as used herein includes any data describing any microorganism and/or combination of microorganisms living on or within a person, including without limitation biomarkers, genomic data, proteomic data, and/or any other metabolic or biochemical data useful for analysis of the effect of such microorganisms on other physiological state data of a person, and/or on prognostic labels and/or ameliorative processes as described in further detail below. With continued reference to FIG. 1, genetics test data 116 may include, without limitation any result of any medical test, physiological assessment, cognitive assessment, psychological assessment, nutritional, or the like. For instance, a user may have completed a nutritional assessment that may determine the nutritional behaviors and patterns of a user. Nutritional behaviors and patterns may include, but are not limited to, types of foods the user likes and/or dislikes; preferred beverages consumed with the types of foods; preferred consumption schedule; preferred substitutions for the types of foods a user likes; foods that may make the user feel unwell; known food allergies, such as a peanut allergy; known food illnesses, such as, but not limited to lactose intolerance; the general health condition of the user, and the like. In an embodiment, based on the nutritional assessment from the user, computing device 104 may output an adverse effect of nutrition on the genetic disorder. For instance, a nutritional assessment may include a favorite type of food such as green vegetables which may include kale or broccoli. As a single gene, TAS2R38, may be responsible for a user's ability to taste phenylthiocarbamide contained in such green vegetables. Computing device 104 may output that those types of vegetables may be tasteless or very bitter as a result of a genetic disorder where TAS2R38 is missing or express incorrectly. The absorption of certain vitamins can also be affected by genetics, such as increased iron absorption in hemochromatosis, a disorder where the body's iron levels build up and overload. people with hemochromatosis possess a gene variant on the short arm of chromosome 6, which is linked to HLA Locus A, and which allows increased iron absorption. A user preferring to eat red meat or raw seafood may be cautioned that consumption of such foods may have an adverse impact on hemochromatosis, if a user has been diagnosed with such disorder. Input 112 may include at least a genetic test data 116 from one or more other devices after performance; system 100 may alternatively or additionally perform one or more assessments and/or tests to obtain at least a genetic test data 116, and/or one or more portions thereof, on system 100. For instance, at least genetics test data 116 may include or more entries by a user in a form or similar graphical user interface object; one or more entries may include, without limitation, user responses to questions on a psychological, behavioral, personality, or cognitive test. For instance, at least a computing device 104 may present to user a set of assessment questions designed or intended to evaluate a current state of mind of the user, a current psychological state of the user, a personality trait of the user, or the like; at least a computing device 104 may provide user-entered responses to such questions directly as at least a genetic test data 116 and/or may perform one or more calculations or other algorithms to derive a score or other result of an assessment as specified by one or more testing protocols, such as automated calculation of a Stanford-Binet and/or Wechsler scale for IQ testing, a personality test scoring such as a Myers-Briggs test protocol, or other assessments that may occur to persons skilled in the art upon reviewing the entirety of this disclosure.

With continued reference to FIG. 1, assessment and/or self-assessment data, and/or automated or other assessment results, obtained from a third-party device; third-party device may include, without limitation, a server or other device (not shown) that performs automated cognitive, psychological, behavioral, personality, or other assessments. Third-party device may include a device operated by an informed advisor. An informed advisor may include any medical professional who may assist and/or participate in the medical treatment of a user. An informed advisor may include a medical doctor, nurse, physician assistant, pharmacist, yoga instructor, nutritionist, spiritual healer, meditation teacher, fitness coach, health coach, life coach, and the like.

With continued reference to FIG. 1, user body measurements may be related to particular dimensions of the human body. A "dimension of the human body" as used in this disclosure, includes one or more functional body systems that are impaired by disease in a human body and/or animal body. Functional body systems may include one or more body systems recognized as attributing to root causes of disease by functional medicine practitioners and experts. A "root cause" as used in this disclosure, includes any chain of causation describing underlying reasons for a particular disease state and/or medical condition instead of focusing solely on symptomatology reversal. Root cause may include chains of causation developed by functional medicine practices that may focus on disease causation and reversal. For instance and without limitation, a medical condition such as diabetes may include a chain of causation that does not include solely impaired sugar metabolism but that also includes impaired hormone systems including insulin resistance, high cortisol, less than optimal thyroid production, and low sex hormones. Diabetes may include further chains of causation that include inflammation, poor diet, delayed food allergies, leaky gut, oxidative stress, damage to cell membranes, and dysbiosis. Dimensions of the human body may include but are not limited to epigenetics, gut-wall, microbiome, nutrients, genetics, and/or metabolism.

With continued reference to FIG. 1, epigenetic, as used herein, includes any user body measurements describing changes to a genome that do not involve corresponding changes in nucleotide sequence. Epigenetic body measurement may include data describing any heritable phenotypic. Phenotype, as used herein, include any observable trait of a user including morphology, physical form, and structure. Phenotype may include a user's biochemical and physiological properties, behavior, and products of behavior. Behavioral phenotypes may include cognitive, personality, and behavior patterns. This may include effects on cellular and physiological phenotypic traits that may occur due to external or environmental factors. For example, DNA methylation and histone modification may alter phenotypic expression of genes without altering underlying DNA sequence. Epigenetic body measurements may include data describing one or more states of methylation of genetic material.

Additionally, and with continued reference to FIG. 1, genetics test data 116 may include data from a biochemical genetic test. As used in this disclosure, a "biochemical genetic test" is a test that includes a study of enzymes and proteins, chromosomes, and genes where the function of the enzymes and proteins, chromosomes, and genes may be abnormal. In one embodiment, genetics test data 116 may include results of a diagnostic genetic testing which, as used in this disclosure, may be used to identify or discard a specific genetic or chromosomal disorder. The specific genetic or chromosomal disorder may be suspected based on physical symptoms or signs. Diagnostic genetic testing may be performed at any time in a person's life which may include in utero. Additionally, biochemical genetic testing may be performed, for instance but not limited to, a blood sample, a urine sample, spinal fluid, amniotic fluid, or in any tissue sample. One example of biochemical genetic testing methods includes molecular genetic testing. Molecular genetic testing includes testing a single gene or short strands of DNA to identify at least one variation or at least one mutation that may lead to a generic disorder. Techniques used in molecular genetic testing include, but are not limited to, a polymerase chain reaction test ("PCR"), DNA sequencing, microarray testing, gene expression profiling, and the like. Another example of a biochemical genetic testing method may include chromosomal genetic testing. Chromosomal genetic testing analyzes whole chromosomes or long strands of DNA to check for large genetic changes, which may include, but are not limited to, an extra copy of a chromosome that may lead to a genetic disorder. Techniques used in chromosomal genetic testing include but are not limited to cytogenetics which may include karyotyping and fluorescence in situ hybridization ("FISH"). A further example of a biochemical genetic testing methods may include the use of immunoassays in the detection of a genetic disorder. Immunoassays are tests based on a very specific binding that occurs between an immunoglobulin or an antibody—a protein produced by the immune system to recognize, bind to, and neutralize a foreign substance in the body—and the substance that it specifically recognizes, such as the foreign substance or an antigen, in the, for example, blood, urine, spinal, or amniotic fluid sample. Combinations of the above-referenced techniques may be used to detect genetic disorders. As a non-limiting illustrative example, an immunoassay for detecting a specific genetic syndrome may be combined with genotyping on a DNA chain amplified with the use of PCR to detect an abnormal sequence that may result in a genetic disorder.

With continued reference to FIG. 1, computing device 104 identifies a plurality of biological indices 120 based on the genetics test data. Plurality of biological indices 120 includes at least one biological index related to a disease state. A "disease state" as used in this disclosure, includes any harmful deviation from the normal structural and/or function state of a human being. A disease state may include any medical condition and may be associated with specific symptoms and signs. A disease state may be classified into different types including infectious diseases, deficiency diseases, hereditary diseases, and/or physiological diseases. For instance, and without limitation, internal dysfunction of the immune system may produce a variety of different diseases including immunodeficiency, hypersensitivity, allergies, and/or autoimmune disorders. The disease state includes at least one genetic disorder. A "genetic disease state," as used in this disclosure, is a disease state that involves any mutation or change of a user that may adversely affect the user and cause a genetic disorder. As used in this disclosure, a "genetic disorder" is a disease state caused in whole or in part by a change in the DNA sequence away from the normal sequence. Genetic disorders may be caused by a mutation in one gene (monogenic disorder), by mutations in multiple genes (multifactorial inheritance disorder), by a combination of gene mutations and environmental factors, or by damage to chromosomes (changes in the number or structure of entire chromosomes, the structures that carry genes). Examples related to genetic disorders may include hemophilia A, where the gene responsible for producing factor VIII is mutated. This mutation, for example, would affect the ability for a user's blood to clot. Another example may include a disease state such as Down Syndrome. A user with Down Syndrome has extra material from chromosome no. 21 which cause a change in the development of the embryo resulting in potential physical and mental abnormalities. The most common error in chromosome replication is "trisomy 21", where the new cell gets three copies of chromosome 21, instead of two. Additionally, a "biological index," as used in this disclosure, is a biological entity found in any body fluid, for example blood, skin sample, or the like, that indicates the presence or absence of a disorder or a disease. A biological index may be classified as, for example, a monitoring biological indicator. A "monitoring biological indicator," as used in this specification, is a biological index that may be used to assess the progress of a disease or to monitor the effects of a therapeutic agent, such as, for example, a platelet-rich plasma treatment. In another example, a biological index may be a diagnostic biological index. A "diagnostic biological index," as defined in this disclosure is a biological index that is used to detect the presence of a disease or a disorder of interest. In an embodiment, the plurality of biological index comprises a diagnostic indicator. Another example of a biological index is a predictive biological index. A "predictive biological index," as used in this disclosure, is a biological indicator used to predict what group of patients will respond favorably or unfavorably to a particular treatment. Examples of biological index that may be used in diagnosing a genetic disorder may include but are not limited to Receptor tyrosine Kinase (9RTK), FGFR-3, EGFR<ERBB2, HER2, ERBB3, NMDA receptor upregulation, repressive H3K9me2, EHMT1, CRIN1, and the like.

Alternatively or additionally, and with continued reference to FIG. 1, in an embodiment, computing device 104 may be configured to analyze a progression of the genetic disorder as a function of the at least one biological index. For instance, a potential underlying genetic cause of Duchenne Muscular Dystrophy ("DMD") may be the presence of a variety of DMD gene mutations that result in dystrophin reduction or absence in skeletal muscle. Using a technique such as microarray-based expression profiling to identify and quantitate the levels of dystrophin in skeletal tissue, computing device 104 may analyze the levels of dystrophin in a control sample and a tissue sample. By comparing the levels of the biological index, dystrophin in this case, between the control sample and the actual tissue sample, a diagnosis and/or progression of a disease, such as DMD may be determined. Similarly, a plurality of biological indices may be analyzed using microarray-based expression profiling or other techniques where their presence and/or absence may determine a diagnosis for the disease or, if the test is positive for a disease, how far has the diseased progress.

Still referring to FIG. 1, computing device 104 may generate a genetic disorder classifier 124. Computing device 104 may generate genetic disorder classifier 124 by receiving genetic disorder training data 128. "Training data," as used herein, is data containing correlations that a machine-learning process may use to model relationships between two or more categories of data elements. For instance, and without limitation, training data such as genetic disorder training data 128 may include a plurality of data entries, each entry representing a set of data elements that were recorded, received, and/or generated together; data elements may be correlated by shared existence in a given data entry, by proximity in a given data entry, or the like. Multiple data entries in training data 128 may evince one or more trends in correlations between categories of data elements; for instance, and without limitation, a higher value of a first data element belonging to a first category of data element may tend to correlate to a higher value of a second data element belonging to a second category of data element, indicating a possible proportional or other mathematical relationship linking values belonging to the two categories. Multiple categories of data elements may be related in training data 128 according to various correlations; correlations may indicate causative and/or predictive links between categories of data elements, which may be modeled as relationships such as mathematical relationships by machine learning processes as described in further detail below. Training data 128 may be formatted and/or organized by categories of data elements, for instance by associating data elements with one or more descriptors corresponding to categories of data elements. As a non-limiting example, training data 128 may include data entered in standardized forms by persons or processes, such that entry of a given data element in a given field in a form may be mapped to one or more descriptors of categories. Elements in training data 128 may be linked to descriptors of categories by tags, tokens, or other data elements; for instance, and without limitation, training data 128 may be provided in fixed-length formats, formats linking positions of data to categories such as comma-separated value (CSV) formats and/or self-describing formats such as extensible markup language (XML), enabling processes or devices to detect categories of data.

Alternatively or additionally, and with continued reference to FIG. 1, training data 128 may include one or more elements that are not categorized; that is, training data 128 may not be formatted or contain descriptors for some elements of data. Machine learning algorithms and/or other processes may sort training data 128 according to one or more categorizations using, for instance, natural language processing algorithms, tokenization, detection of correlated values in raw data and the like; categories may be generated using correlation and/or other processing algorithms. As a non-limiting example, in a corpus of text, phrases making up a number "n" of compound words, such as nouns modified by other nouns, may be identified according to a statistically significant prevalence of n-grams containing such words in a particular order; such an n-gram may be categorized as an element of language such as a "word" to be tracked similarly to single words, generating a new category as a result of statistical analysis. Similarly, in a data entry including some textual data, a person's name may be identified by reference to a list, dictionary, or other compendium of terms, permitting ad-hoc categorization by machine learning algorithms, and/or automated association of data in the data entry with descriptors or into a given format. The ability to categorize data entries automatedly may enable the same training data 128 to be made applicable for two or more distinct machine learning algorithms as described in further detail below. Training data 128 used by computing device 104 may correlate any input data as described in this disclosure to any output data as described in this disclosure. Training data may contain entries, each of which correlates a machine learning process input to a machine learning process output, for instance without limitation, one or more elements of biological extraction data to a taste index. Training data may be obtained from previous iterations of machine-learning processes, user inputs, and/or expert inputs. For example, genetic disorder training data 128 correlates biological indices of genetic disorder and genetic markers to genetic disorder labels. As used in this disclosure, a "genetic marker" is a DNA sequence with a known physical location on a chromosome. Genetic markers may link a genetic disorder with a responsible gene. Examples of genetic markers include but are not limited to Restriction fragment length polymorphism (RFLP), single nucleotide polymorphism (SNP), restriction site associated DNA markers (RAD markers), and the like. For example, an SNP is the substitution of a C for a G in the nucleotide sequence AACGAT, thereby producing the sequence AACCAT. SNPs may act as chromosomal tags to specific regions of DNA, and these regions can be scanned for variations that may be involved in a genetic disorder. Such SNPs associated with a genetic disorder may be used as diagnostic tool. Additionally, "genetic disorder labels," as used in this disclosure, are genetic disorders that may be used to tag a genetic disorder. For example in children, fetal hemoglobin (HbF) at 10% concentration and α-thalassemia are the two well-studied biomarkers in sickle cell anemia. An SNP may identify a single nucleotide difference in a healthy phenotype of a DNA sequence of the hemoglobin HBB gene (G-A-G) in contrast to an affected phenotype at the same location (G-T-G). For example, the presence of HbF and α-thalassemia in addition to the presence of the abnormal phenotype may be tagged with "Sickle Cell Anemia." Computing device 104 may train genetic disorder classifier 124 using genetic disorder training data 128.

Still with reference to FIG. 1, computing device 104 may classify, using genetic disorder classifier 124, at least one biological index and at least one genetic marker to a positive result for a genetic disorder. A "positive result" for a genetic disorder, as defined by this disclosure, is a test result where at least one biological indicator for a genetic disorder may be found. A positive result may indicate that the user may be presently suffering from a genetic disorder. Alternatively, a positive result may also indicate that the user may develop a genetic disorder in the future. For example, a positive test for breast cancer may indicate that biological indices BRCA1 and BRCA2 are present. A positive result may be obtained based a population screening test conducted to identify asymptomatic individuals from within a particular community or a subsection of that community who have an increased chance of having a specific genetic disorder, of carrying a specific genetic predisposition to disease or of being a carrier of a recessive genetic variant. A description on machine learning and the use of classifiers follows below.

Figure 3:
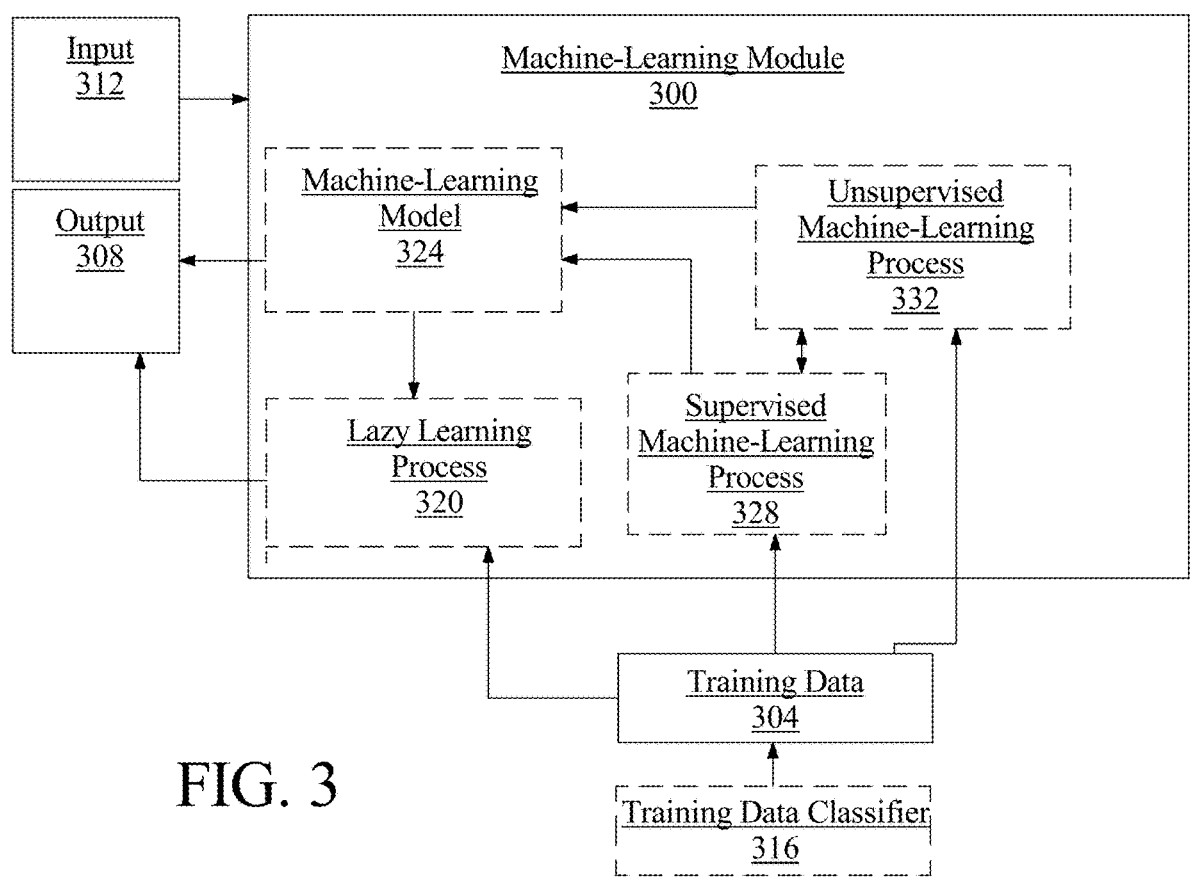
FIG. 3 is a block diagram of an exemplary embodiment of a machine-learning module.

Referring now to FIG. 3, an exemplary embodiment of a machine-learning module 300 that may perform one or more machine-learning processes as described in this disclosure is illustrated. Machine-learning module may perform determinations, classification, and/or analysis steps, methods, processes, or the like as described in this disclosure using machine learning processes. A "machine learning process," as used in this disclosure, is a process that automatedly uses training data 304 to generate an algorithm that will be performed by a computing device/module to produce outputs 308 given data provided as inputs 312; this contrasts with a non-machine learning software program where the commands to be executed are determined in advance by a user and written in a programming language.

Still referring to FIG. 3, "training data," as used herein, is data containing correlations that a machine-learning process may use to model relationships between two or more categories of data elements. For instance, and without limitation, training data 304 may include a plurality of data entries, each entry representing a set of data elements that were recorded, received, and/or generated together; data elements may be correlated by shared existence in each data entry, by proximity in a given data entry, or the like. Multiple data entries in training data 304 may evince one or more trends in correlations between categories of data elements; for instance, and without limitation, a higher value of a first data element belonging to a first category of data element may tend to correlate to a higher value of a second data element belonging to a second category of data element, indicating a possible proportional or other mathematical relationship linking values belonging to the two categories. Multiple categories of data elements may be related in training data 304 according to various correlations; correlations may indicate causative and/or predictive links between categories of data elements, which may be modeled as relationships such as mathematical relationships by machine-learning processes as described in further detail below. Training data 304 may be formatted and/or organized by categories of data elements, for instance by associating data elements with one or more descriptors corresponding to categories of data elements. As a non-limiting example, training data 304 may include data entered in standardized forms by persons or processes, such that entry of a given data element in a given field in a form may be mapped to one or more descriptors of categories. Elements in training data 304 may be linked to descriptors of categories by tags, tokens, or other data elements; for instance, and without limitation, training data 304 may be provided in fixed-length formats, formats linking positions of data to categories such as comma-separated value (CSV) formats and/or self-describing formats such as extensible markup language (XML), JavaScript Object Notation (JSON), or the like, enabling processes or devices to detect categories of data.

Alternatively or additionally, and continuing to refer to FIG. 3, training data 304 may include one or more elements that are not categorized; that is, training data 304 may not be formatted or contain descriptors for some elements of data. Machine-learning algorithms and/or other processes may sort training data 304 according to one or more categorizations using, for instance, natural language processing algorithms, tokenization, detection of correlated values in raw data and the like; categories may be generated using correlation and/or other processing algorithms. As a non-limiting example, in a corpus of text, phrases making up a number "n" of compound words, such as nouns modified by other nouns, may be identified according to a statistically significant prevalence of n-grams containing such words in a particular order; such an n-gram may be categorized as an element of language such as a "word" to be tracked similarly to single words, generating a new category because of statistical analysis. Similarly, in a data entry including some textual data, a person's name may be identified by reference to a list, dictionary, or other compendium of terms, permitting ad-hoc categorization by machine-learning algorithms, and/or automated association of data in the data entry with descriptors or into a given format. The ability to categorize data entries automatedly may enable the same training data 304 to be made applicable for two or more distinct machine-learning algorithms as described in further detail below. Training data 304 used by machine-learning module 300 may correlate any input data as described in this disclosure to any output data as described in this disclosure. As a non-limiting illustrative example, genetic disorder biological indices may serve as inputs, outputting other potential health disorders that a may use the same and/or related biological indices.

Further referring to FIG. 3, training data may be filtered, sorted, and/or selected using one or more supervised and/or unsupervised machine-learning processes and/or models as described in further detail below; such models may include without limitation a training data classifier 316. Training data classifier 316 may include a "classifier," which as used in this disclosure is a machine-learning model as defined below, such as a mathematical model, neural net, or program generated by a machine learning algorithm known as a "classification algorithm," as described in further detail below, that sorts inputs into categories or bins of data, outputting the categories or bins of data and/or labels associated therewith. A classifier may be configured to output at least a datum that labels or otherwise identifies a set of data that are clustered together, found to be close under a distance metric as described below, or the like. Machine-learning module 300 may generate a classifier using a classification algorithm, defined as a process whereby a computing device and/or any module and/or component operating thereon derives a classifier from training data 304. Classification may be performed using, without limitation, linear classifiers such as without limitation logistic regression and/or naive Bayes classifiers, nearest neighbor classifiers such as k-nearest neighbors classifiers, support vector machines, least squares support vector machines, fisher's linear discriminant, quadratic classifiers, decision trees, boosted trees, random forest classifiers, learning vector quantization, and/or neural network-based classifiers. As a non-limiting example, training data classifier 316 may classify elements of training data to classify a genetic disorder into categories such as a single gene disorders, complex gene disorders, chromosomal disorders, and the like.

Still referring to FIG. 3, machine-learning module 300 may be configured to perform a lazy-learning process 320 and/or protocol, which may alternatively be referred to as a "lazy loading" or "call-when-needed" process and/or protocol, may be a process whereby machine learning is conducted upon receipt of an input to be converted to an output, by combining the input and training set to derive the algorithm to be used to produce the output on demand. For instance, an initial set of simulations may be performed to cover an initial heuristic and/or "first guess" at an output and/or relationship. As a non-limiting example, an initial heuristic may include a ranking of associations between inputs and elements of training data 304. Heuristic may include selecting some number of highest-ranking associations and/or training data 304 elements. Lazy learning may implement any suitable lazy learning algorithm, including without limitation a K-nearest neighbors algorithm, a lazy naïve Bayes algorithm, or the like; persons skilled in the art, upon reviewing the entirety of this disclosure, will be aware of various lazy-learning algorithms that may be applied to generate outputs as described in this disclosure, including without limitation lazy learning applications of machine-learning algorithms as described in further detail below.

Alternatively or additionally, and with continued reference to FIG. 3, machine-learning processes as described in this disclosure may be used to generate machine-learning models 324. A "machine-learning model," as used in this disclosure, is a mathematical and/or algorithmic representation of a relationship between inputs and outputs, as generated using any machine-learning process including without limitation any process as described above and stored in memory; an input is submitted to a machine-learning model 324 once created, which generates an output based on the relationship that was derived. For instance, and without limitation, a linear regression model, generated using a linear regression algorithm, may compute a linear combination of input data using coefficients derived during machine-learning processes to calculate an output datum. As a further non-limiting example, a machine-learning model 324 may be generated by creating an artificial neural network, such as a convolutional neural network comprising an input layer of nodes, one or more intermediate layers, and an output layer of nodes. Connections between nodes may be created via the process of "training" the network, in which elements from a training data 304 set are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning.

Still referring to FIG. 3, machine-learning algorithms may include at least a supervised machine-learning process 328. At least a supervised machine-learning process 328, as defined herein, include algorithms that receive a training set relating a number of inputs to a number of outputs, and seek to find one or more mathematical relations relating inputs to outputs, where each of the one or more mathematical relations is optimal according to some criterion specified to the algorithm using some scoring function. For instance, a supervised learning algorithm may include a biological index such as interleukin (IL)-6 as described above as inputs, with at least rheumatoid arthritis as an output of a genetic disorder, and a scoring function representing a desired form of relationship to be detected between inputs and outputs; scoring function may, for instance, seek to maximize the probability that a given input and/or combination of elements inputs is associated with a given output to minimize the probability that a given input is not associated with a given output. Scoring function may be expressed as a risk function representing an "expected loss" of an algorithm relating inputs to outputs, where loss is computed as an error function representing a degree to which a prediction generated by the relation is incorrect when compared to a given input-output pair provided in training data 304. Persons skilled in the art, upon reviewing the entirety of this disclosure, will be aware of various possible variations of at least a supervised machine-learning process 328 that may be used to determine relation between inputs and outputs. Supervised machine-learning processes may include classification algorithms as defined above.

Further referring to FIG. 3, machine learning processes may include at least an unsupervised machine-learning processes 332. An unsupervised machine-learning process, as used herein, is a process that derives inferences in datasets without regard to labels; as a result, an unsupervised machine-learning process may be free to discover any structure, relationship, and/or correlation provided in the data. Unsupervised processes may not require a response variable; unsupervised processes may be used to find interesting patterns and/or inferences between variables, to determine a degree of correlation between two or more variables, or the like.

Still referring to FIG. 3, machine-learning module 300 may be designed and configured to create a machine-learning model 324 using techniques for development of linear regression models. Linear regression models may include ordinary least squares regression, which aims to minimize the square of the difference between predicted outcomes and actual outcomes according to an appropriate norm for measuring such a difference (e.g. a vector-space distance norm); coefficients of the resulting linear equation may be modified to improve minimization. Linear regression models may include ridge regression methods, where the function to be minimized includes the least-squares function plus term multiplying the square of each coefficient by a scalar amount to penalize large coefficients. Linear regression models may include least absolute shrinkage and selection operator (LASSO) models, in which ridge regression is combined with multiplying the least-squares term by a factor of 1 divided by double the number of samples. Linear regression models may include a multi-task lasso model wherein the norm applied in the least-squares term of the lasso model is the Frobenius norm amounting to the square root of the sum of squares of all terms. Linear regression models may include the elastic net model, a multi-task elastic net model, a least angle regression model, a LARS lasso model, an orthogonal matching pursuit model, a Bayesian regression model, a logistic regression model, a stochastic gradient descent model, a perceptron model, a passive aggressive algorithm, a robustness regression model, a Huber regression model, or any other suitable model that may occur to persons skilled in the art upon reviewing the entirety of this disclosure. Linear regression models may be generalized in an embodiment to polynomial regression models, whereby a polynomial equation (e.g. a quadratic, cubic or higher-order equation) providing a best predicted output/actual output fit is sought; similar methods to those described above may be applied to minimize error functions, as will be apparent to persons skilled in the art upon reviewing the entirety of this disclosure.

Continuing to refer to FIG. 3, machine-learning algorithms may include, without limitation, linear discriminant analysis. Machine-learning algorithm may include quadratic discriminate analysis. Machine-learning algorithms may include kernel ridge regression. Machine-learning algorithms may include support vector machines, including without limitation support vector classification-based regression processes. Machine-learning algorithms may include stochastic gradient descent algorithms, including classification and regression algorithms based on stochastic gradient descent. Machine-learning algorithms may include nearest neighbors algorithms. Machine-learning algorithms may include Gaussian processes such as Gaussian Process Regression. Machine-learning algorithms may include cross-decomposition algorithms, including partial least squares and/or canonical correlation analysis. Machine-learning algorithms may include naïve Bayes methods. Machine-learning algorithms may include algorithms based on decision trees, such as decision tree classification or regression algorithms. Machine-learning algorithms may include ensemble methods such as bagging meta-estimator, forest of randomized tress, AdaBoost, gradient tree boosting, and/or voting classifier methods. Machine-learning algorithms may include neural net algorithms, including convolutional neural net processes.

Referring back to FIG. 1, in an embodiment, computing device 104 may receive disease training data and train a machine-learning model using the disease training data. The disease training data correlates biological indices of genetic disorders with related disease states. As used in this disclosure, a "related disease state" refers to a disease state that may share a biological index with another disease state or may indicate a predisposition for another disease state. As a non-limiting example, a lymphoblastoid expression of the proteins ORMDL3 and GSDML may show an association with asthma. Another non-limiting example may include a variant of MAPT that is associated with progressive supranuclear palsy which is also associated with MAPT mRNA expression. Computing device 104 may output a plurality of related disease states based on the machine-learning model. One of ordinary skill would understand after reviewing the entire content of this disclosure other possible associations between a biological index and a related disease state. By employing optimization methods involving machine-learning models to generate the associations between a biological index and a related disease state, such analysis may show a person's predisposition to another category of disease such as cardiovascular disease, cancer, pulmonary disease, neurological disease, endocrine disease, viral outbreaks, digestive disease, psychiatric disease, autoimmune disease, bacterial infections, blood diseases, congenital diseases, connective tissue disease, ears/nose/throat diseases, eye diseases, reproductive diseases, immune system diseases, urinary diseases, metabolic disorders, musculoskeletal diseases, parasitic diseases, skin diseases, body degradation, body inflammation, and the like.

With continued reference to FIG. 1, computing device 104 may generate sustenance plan 132 as a function of the positive result. As defined in this disclosure, a "sustenance plan" is an instruction set for consumption of a plurality of sustenance compositions which, as used in this disclosure, may help relieve and/or slow the progression of, for example, a genetic disorder. "Sustenance compositions," as used in this disclosure, may include any combination of ingredients that may be treated as a meal or a snack or any beverages or combination of beverages that may be consumed by a user. Sustenance plan 132 may include, for example, what type of sustenance compositions a user may want to consume based on the desire to relieve and/or prevent a genetic disorder. Sustenance plan 132 may include what specific time of the day the user should consume the sustenance compositions. Sustenance plan 132 may include a list of sustenance compositions to avoid based on a genetic disorder. Sustenance plan 132 may include a list of acceptable sustenance compositions substitutes in case a sustenance composition suggested to the user is not available. Sustenance plan 132 may include a list of nutritional supplements that may relieve and/or prevent one or more genetic disorders. Sustenance plan 132 may include information as to how to safely take the supplements as well as information regarding any potential adverse effects.

Additionally or alternatively, with reference to FIG. 1, computing device 104 may be configured to generate the sustenance plan based on the plurality of related disease states and the genetic disorder. For instance, Phenylketonuria (PKU) is a type of amino acid metabolism disorder preventing the metabolism of phenylalanine (Phe). A low-protein diet may help manage Phenylketonuria. Similarly, a low-protein diet may help manage a disease state related to phenylketonuria which may affects the kidneys. Examples of a low protein sustenance plan may include the consumption of fruits such as bananas and any type of berries; vegetables such as leafy green vegetables, peppers, broccoli, and the like; and grains such as rice, oats, barley, and the like.

Referring still to FIG. 1, computing device 104 may be configured to receive a second input. The second input may include any of the inputs as described for input 112. For example, a second input may correspond to a second sample taken after commencing use of sustenance plan 132. A medical professional may want to retest a user to check for changes in the presence or absence of biological index 120. Computing device 104 may reclassify at least one biological index and the at least one genetic marker from the second input to a positive result of the genetic disorder. Computing device 104 may update the alimentary plan as a function of the second input. As a non-limiting example, SNPs related to obesity, such as FTO and MC4R may still be present in a genetic test. Sustenance plan 132 generated to address a person's weight, may contain but not limited to an increase in the consumption of fruits and vegetables and a reduction in the caloric intake suggested by a decrease in the meal size. Sustenance plan 132 may be updated to, for example, further reduce the caloric intake and increase the consumption of fiber.

Figure 4:
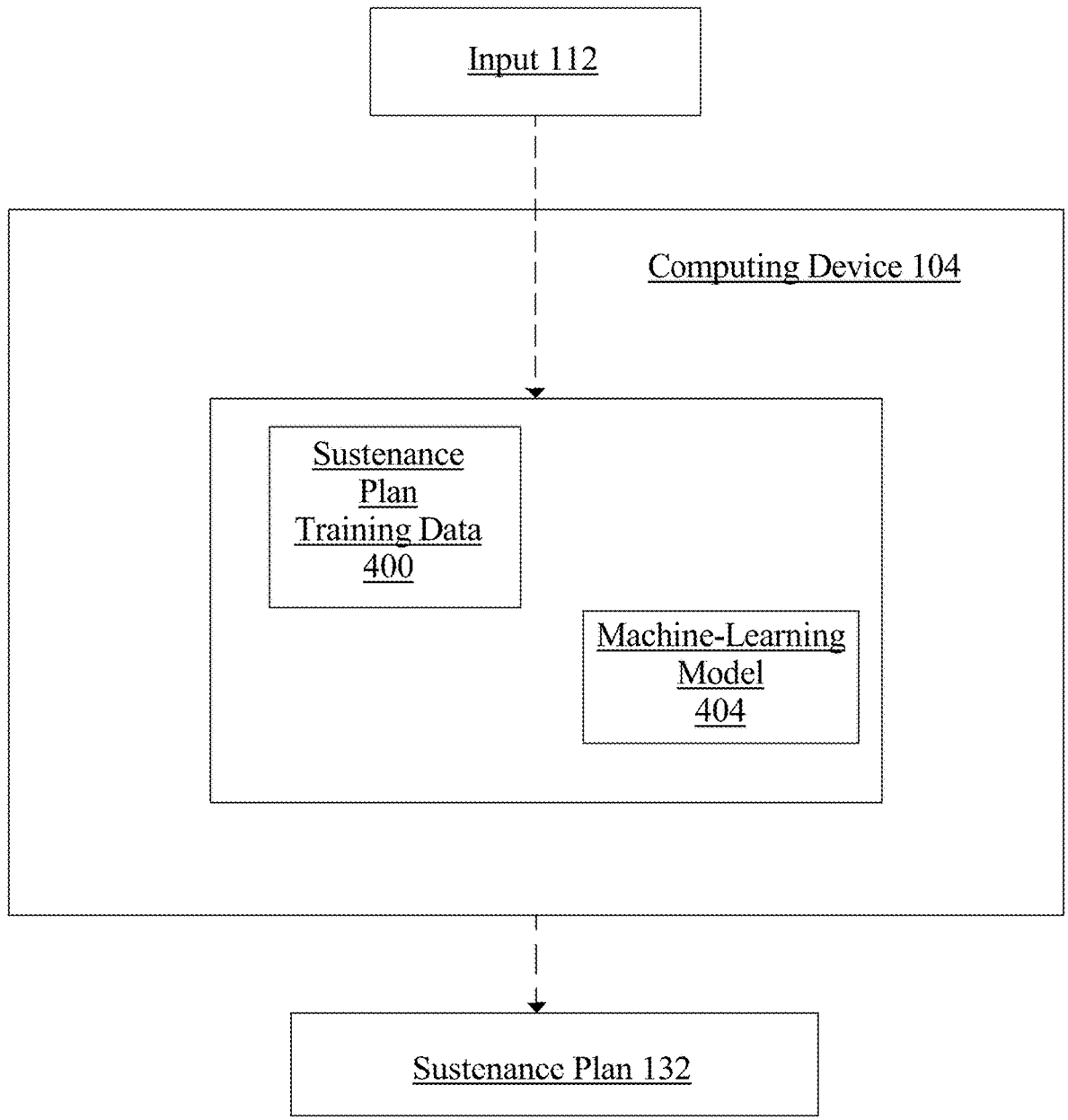
FIG. 4 is a block diagram of an exemplary embodiment of a determination of a sustenance plan as a function of a machine-learning process.

Now referring to FIG. 4, an exemplary embodiment of the generation of sustenance plan 132 implementing a machine learning model is described. Computing device 104 is configured to receive input 112. Computing device 104 may receive sustenance plan training data 400. Sustenance plan training data 400 may be received and/or collected by experts or collected from users that may have received and used an alimentary plan. Sustenance plan training data 400 may be received as a function of user-entered valuations of sustenance plans, sustenance plan metrics, and/or measurable values. The vector training set may be received by one or more past iterations of the previous sustenance plan vectors. The vector training set may be received by one or more remote devices that at least correlate a sustenance plan element and genetic disorder metric to a measurable value, wherein a remote device is an external device to computing device 104. A machine-learning model 404 is trained using sustenance plan training data 400. Sustenance plan training data 400 correlates sustenance plans with a historical ameliorative effect on a genetic disorder. For example, sustenance training data 400 would include those sustenance plans that have relieved symptoms and/or effects of a genetic disorder. Sustenance plan 132 is outputted as a function of the machine-learning model. The machine-learning model may be implemented, without any limitations, as described earlier in this disclosure. In another embodiment, generating sustenance plan 132 may include outputting a message independent of the presence of the plurality of alimentary plans. For example, sustenance plan training data 400 may not contain values for a particular genetic disorder. As a result, sustenance plan 132 may not be a suitable sustenance plan to treat and/or prevent and/or improve the particular genetic disorder. As such, a message may be outputted indicating this disorder. The message may be outputted directly to a user device, a web page, an email message, and the like. An example of a message may include, "No nutrition suggestions are available for this genetic disorder."

Figure 5:
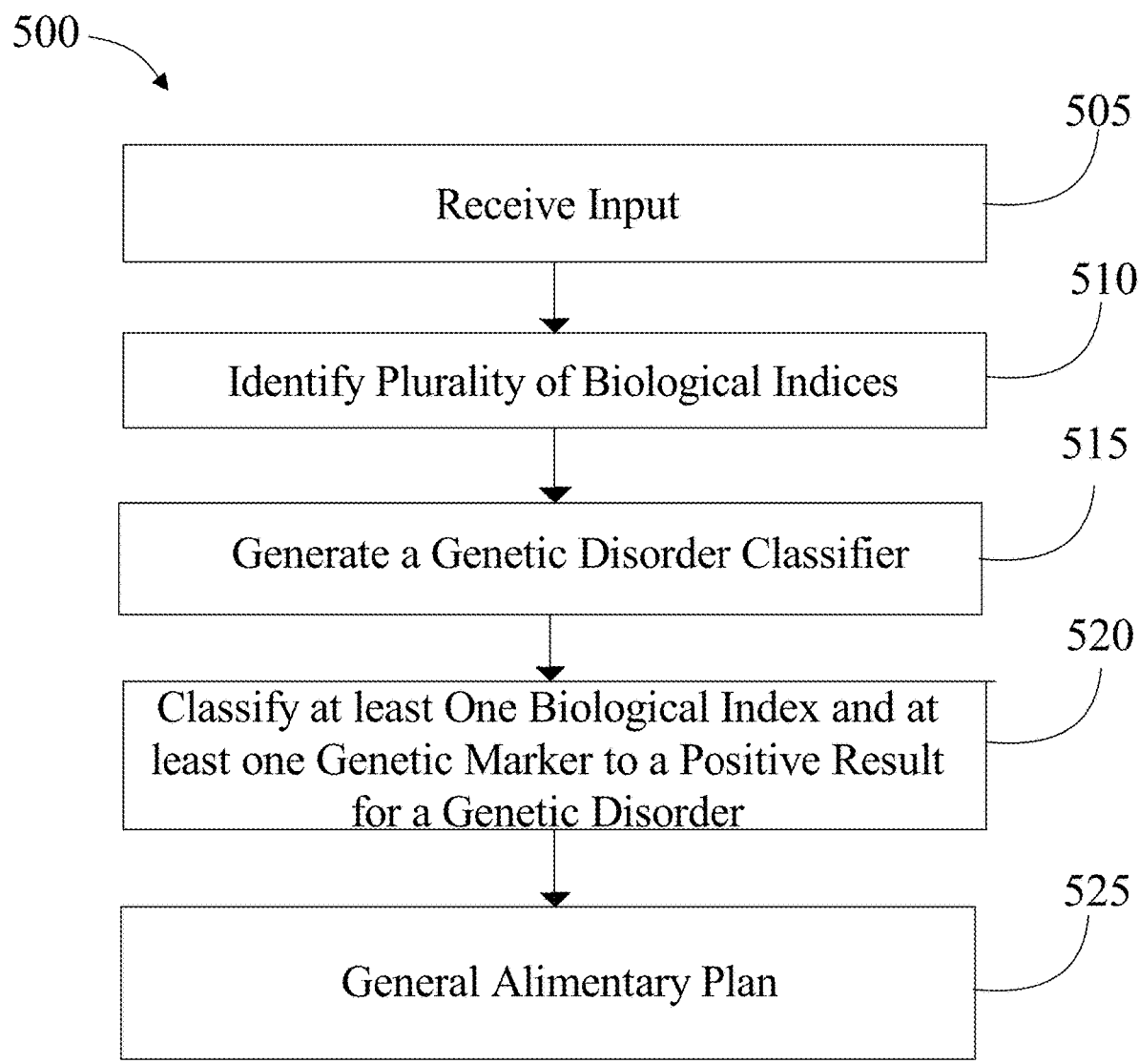
FIG. 5 is a flow diagram illustrating an exemplary embodiment of a method of determining a sustenance plan for managing a genetic disorder.

Referring now to FIG. 5, an exemplary method 500 for generating an alimentary plan to manage a genetic disorder is described. At step 505, a computing device receives an input. The input includes genetics test data, where the genetics test data includes data from a biochemical genetic test. This step may be implemented, without limitation, as described in FIGS. 1-4. The genetics test data may include results of a diagnostic genetic test. The genetics test data may include data from a nutritional assessment. In an embodiment computing device is configured to output an adverse effect on the genetic disorder as a function of the nutritional assessment.

With continued reference to FIG. 5, at step 510, computing device may identify a plurality of biological indices based on the genetics test data. The plurality of biological indices includes at least one biological index based on the genetics test data. This step may be implemented, without limitation, as described in FIGS. 1-4. In an embodiment, computing device may be configured to analyze a progression of the genetic disorder as a function of the at least one biological index.

Still with reference to FIG. 5, at step 515, computing device may generate a genetic disorder classifier. Computing device may generate a genetic disorder classifier by receiving genetic disorder training data correlating biological indices of genetic disorders and genetic markers to genetic disorder labels. Computing device may train genetic disorder classifier using genetic disorder training data. This step may be implemented, without limitation, as described in FIGS. 1-4.

Additionally or alternatively, with continued reference to FIG. 5, computing device may receive disease training data and train a machine-learning model using the disease training data. Computing device may output a plurality of related disease states as a function of the machine-learning model. This may be implemented, without limitations, as described in FIGS. 1-4.

With continued reference to FIG. 5, at step 520, computing device may classify, using genetic disorder classifier at least one biological index and at least one genetic marker to a positive result for a genetic disorder. This step may be implemented, without limitations, as described in FIGS. 1-4.

Still referencing FIG. 5, at step 525, computing device may generate a sustenance plan as a function of the positive result. This step may be implemented, without limitations, as described in FIGS. 1-4. In an embodiment, computing device may be configured to generate a sustenance plan based on the plurality of related disease states and the genetic disorder.

Additionally or alternatively, with continued reference to FIG. 5, in an embodiment, computing device may be configured to receive a second input. Computing device my reclassify at least one biological index and the at least one genetic marker from the second input to a positive result of the genetic disorder. Computing device may update the alimentary plan as a function of the second input. The above may be implemented, without limitation, as described in FIGS. 1-4.

In another embodiment, computing device may receive sustenance plan training data that correlates sustenance plans with a historical ameliorative effect on a genetic disorder. The machine training data may be used to train a machine-learning model. A sustenance plan is outputted as a function of the machine-learning model. In a further embodiment, generating the sustenance plan may include outputting a message independent of the presence of the plurality of alimentary plans. The above may be implemented, without limitation, as described in FIGS. 1-4.

It is to be noted that any one or more of the aspects and embodiments described herein may be conveniently implemented using one or more machines (e.g., one or more computing devices that are utilized as a user computing device for an electronic document, one or more server devices, such as a document server, etc.) programmed according to the teachings of the present specification, as will be apparent to those of ordinary skill in the computer art. Appropriate software coding can readily be prepared by skilled programmers based on the teachings of the present disclosure, as will be apparent to those of ordinary skill in the software art. Aspects and implementations discussed above employing software and/or software modules may also include appropriate hardware for assisting in the implementation of the machine executable instructions of the software and/or software module.

Such software may be a computer program product that employs a machine-readable storage medium. A machine-readable storage medium may be any medium that is capable of storing and/or encoding a sequence of instructions for execution by a machine (e.g., a computing device) and that causes the machine to perform any one of the methodologies and/or embodiments described herein. Examples of a machine-readable storage medium include, but are not limited to, a magnetic disk, an optical disc (e.g., CD, CD-R, DVD, DVD-R, etc.), a magneto-optical disk, a read-only memory "ROM" device, a random-access memory "RAM" device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission.

Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device) and any related information (e.g., data structures and data) that causes the machine to perform any one of the methodologies and/or embodiments described herein.

Examples of a computing device include, but are not limited to, an electronic book reading device, a computer workstation, a terminal computer, a server computer, a handheld device (e.g., a tablet computer, a smartphone, etc.), a web appliance, a network router, a network switch, a network bridge, any machine capable of executing a sequence of instructions that specify an action to be taken by that machine, and any combinations thereof. In one example, a computing device may include and/or be included in a kiosk.

Figure 6:
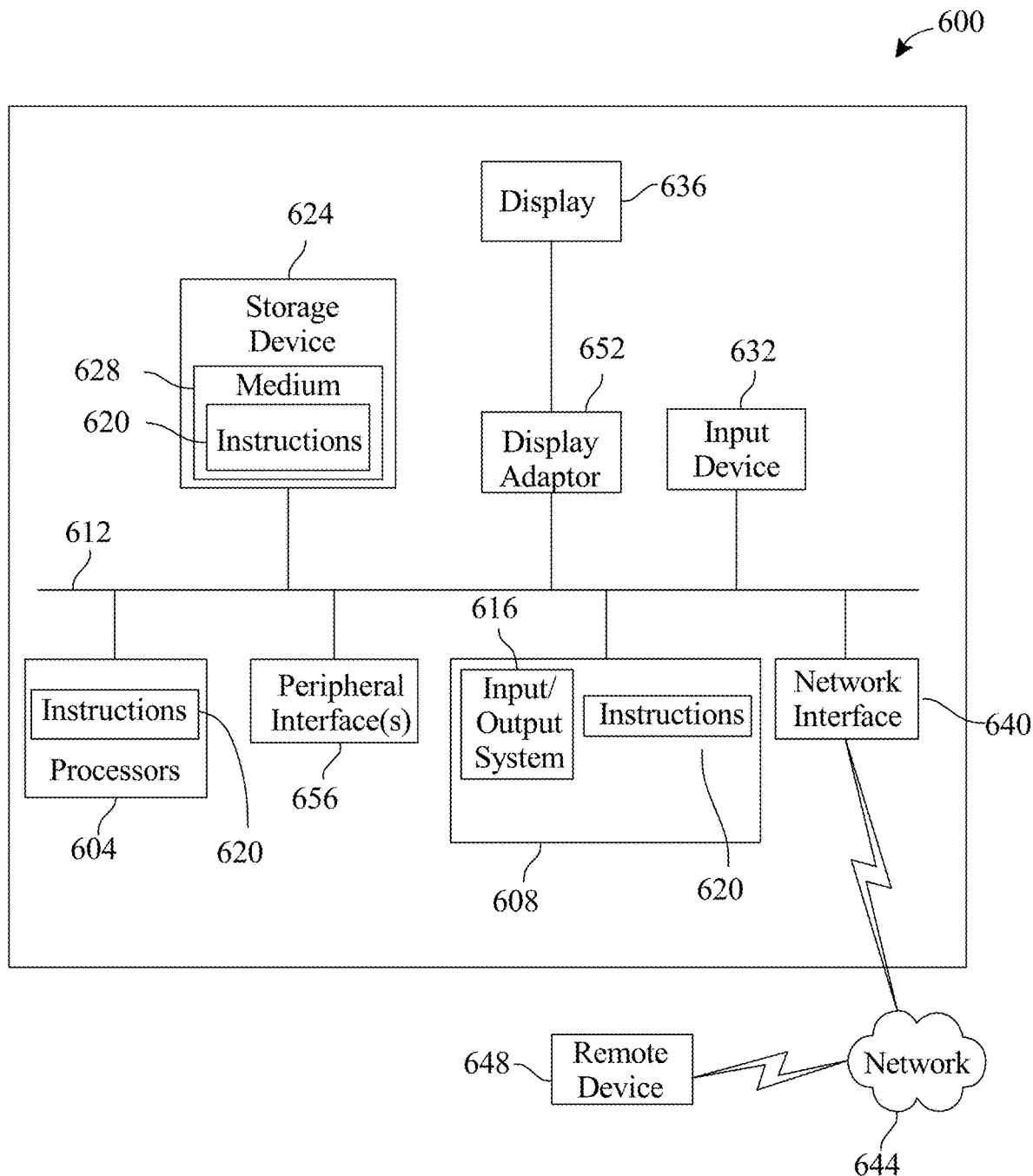
FIG. 6 is a block diagram of a computing system that can be used to implement any one or more of the methodologies disclosed herein and any one or more portions thereof.

FIG. 6 shows a diagrammatic representation of one embodiment of a computing device in the exemplary form of a computer system 600 within which a set of instructions for causing a control system to perform any one or more of the aspects and/or methodologies of the present disclosure may be executed. It is also contemplated that multiple computing devices may be utilized to implement a specially configured set of instructions for causing one or more of the devices to perform any one or more of the aspects and/or methodologies of the present disclosure. Computer system 600 includes a processor 604 and a memory 608 that communicate with each other, and with other components, via a bus 612. Bus 612 may include any of several types of bus structures including, but not limited to, a memory bus, a memory controller, a peripheral bus, a local bus, and any combinations thereof, using any of a variety of bus architectures.

Processor 604 may include any suitable processor, such as without limitation a processor incorporating logical circuitry for performing arithmetic and logical operations, such as an arithmetic and logic unit (ALU), which may be regulated with a state machine and directed by operational inputs from memory and/or sensors; processor 604 may be organized according to Von Neumann and/or Harvard architecture as a non-limiting example. Processor 604 may include, incorporate, and/or be incorporated in, without limitation, a microcontroller, microprocessor, digital signal processor (DSP), Field Programmable Gate Array (FPGA), Complex Programmable Logic Device (CPLD), Graphical Processing Unit (GPU), general purpose GPU, Tensor Processing Unit (TPU), analog or mixed signal processor, Trusted Platform Module (TPM), a floating-point unit (FPU), and/or system on a chip (SoC)

Memory 608 may include various components (e.g., machine-readable media) including, but not limited to, a random-access memory component, a read only component, and any combinations thereof. In one example, a basic input/output system 616 (BIOS), including basic routines that help to transfer information between elements within computer system 600, such as during start-up, may be stored in memory 608. Memory 608 may also include (e.g., stored on one or more machine-readable media) instructions (e.g., software) 620 embodying any one or more of the aspects and/or methodologies of the present disclosure. In another example, memory 608 may further include any number of program modules including, but not limited to, an operating system, one or more application programs, other program modules, program data, and any combinations thereof.

Computer system 600 may also include a storage device 624. Examples of a storage device (e.g., storage device 624) include, but are not limited to, a hard disk drive, a magnetic disk drive, an optical disc drive in combination with an optical medium, a solid-state memory device, and any combinations thereof. Storage device 624 may be connected to bus 612 by an appropriate interface (not shown). Example interfaces include, but are not limited to, SCSI, advanced technology attachment (ATA), serial ATA, universal serial bus (USB), IEEE 1394 (FIREWIRE), and any combinations thereof. In one example, storage device 624 (or one or more components thereof) may be removably interfaced with computer system 600 (e.g., via an external port connector (not shown)). Particularly, storage device 624 and an associated machine-readable medium 628 may provide nonvolatile and/or volatile storage of machine-readable instructions, data structures, program modules, and/or other data for computer system 600. In one example, software 620 may reside, completely or partially, within machine-readable medium 628. In another example, software 620 may reside, completely or partially, within processor 604.

Computer system 600 may also include an input device 632. In one example, a user of computer system 600 may enter commands and/or other information into computer system 600 via input device 632. Examples of an input device 632 include, but are not limited to, an alpha-numeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), a touchscreen, and any combinations thereof. Input device 632 may be interfaced to bus 612 via any of a variety of interfaces (not shown) including, but not limited to, a serial interface, a parallel interface, a game port, a USB interface, a FIREWIRE interface, a direct interface to bus 612, and any combinations thereof. Input device 632 may include a touch screen interface that may be a part of or separate from display 636, discussed further below. Input device 632 may be utilized as a user selection device for selecting one or more graphical representations in a graphical interface as described above.

A user may also input commands and/or other information to computer system 600 via storage device 624 (e.g., a removable disk drive, a flash drive, etc.) and/or network interface device 640. A network interface device, such as network interface device 640, may be utilized for connecting computer system 600 to one or more of a variety of networks, such as network 644, and one or more remote devices 648 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network, such as network 644, may employ a wired and/or a wireless mode of communication. In general, any network topology may be used. Information (e.g., data, software 620, etc.) may be communicated to and/or from computer system 600 via network interface device 640.

Computer system 600 may further include a video display adapter 652 for communicating a displayable image to a display device, such as display device 636. Examples of a display device include, but are not limited to, a liquid crystal display (LCD), a cathode ray tube (CRT), a plasma display, a light emitting diode (LED) display, and any combinations thereof. Display adapter 652 and display device 636 may be utilized in combination with processor 604 to provide graphical representations of aspects of the present disclosure. In addition to a display device, computer system 600 may include one or more other peripheral output devices including, but not limited to, an audio speaker, a printer, and any combinations thereof. Such peripheral output devices may be connected to bus 612 via a peripheral interface 656. Examples of a peripheral interface include, but are not limited to, a serial port, a USB connection, a FIREWIRE connection, a parallel connection, and any combinations thereof.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve methods and systems to the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

What is claimed is:

1. A system for generating a sustenance plan for managing genetic disorders, the system comprising:
   a computing device configured to:
      receive at least one genetic marker and an input comprising genetics test data;
      identify a plurality of biological indices of a disease state as a function of the genetics test data, wherein the plurality of biological indices comprises at least one biological index related to a genetic disease state;
      generate a genetic disorder classifier, wherein the generating the genetic disorder classifier comprises:
         receiving genetic disorder training data correlating biological indices of genetic disorders and genetic markers to genetic disorder labels; and
         training the genetic disorder classifier using the genetic disorder training data;
      input the at least one biological index and the at least one genetic marker into the genetic disorder classifier;
      classify, using the genetic disorder classifier, the at least one biological index and the at least one genetic marker to a positive result for a genetic disorder; and
      generate a sustenance plan as a function of the positive result, wherein generating the sustenance plan further comprises:
         receiving sustenance plan training data;
         training a machine-learning model using the sustenance plan training data, wherein the sustenance plan training data correlates sustenance plans with a historical ameliorative effect on genetic disorders;
         inputting the genetic disorder into the machine-learning model; and
         outputting the sustenance plan as a function of the genetic disorder and the machine-learning model.

2. The system of claim 1, wherein the computing device is further configured to analyze a progression of the genetic disorder as a function of the at least one biological index.

3. The system of claim 1, wherein the computing device is further configured to:
   receive disease training data;
   train a machine-learning model using the disease training data, wherein the disease training data correlates biological indices related to genetic disorders with related disease states; and
   output a plurality of related disease states as a function of the machine-learning model.

4. The system of claim 3, wherein the computing device is further configured to generate the sustenance plan as a function of the plurality of related disease states and the genetic disorder.

5. The system of claim 1, wherein the genetics test data comprises results of a diagnostic genetic testing.

6. The system of claim 1, wherein the genetics test data comprises data from a nutritional assessment.

7. The system of claim 6, wherein the computing device is further configured to output an adverse effect of the nutritional behavior on the genetic disorder as a function of the nutritional assessment.

8. The system of claim 1, wherein generating the sustenance plan further comprises outputting a message independent of a presence of the sustenance plan.

9. The system of claim 1, wherein the computing device is further configured to:
   receive a second input;
   reclassify the at least one biological index and the at least one genetic marker from the second input to a positive result of the genetic disorder; and
   update the sustenance plan as a function of the second input.

10. A method for generating a sustenance plan for managing genetic disorders, the method comprising:
    receiving, by a computing device, at least one genetic marker and an input comprising genetics test data;
    identifying a plurality of biological indices of a disease state as a function of the genetics test data, wherein the plurality of biological indices comprises at least one biological index related to a genetic disease state;
    generating, by the computing device, a genetic disorder classifier, wherein the generating the genetic disorder classifier comprises:
       receiving genetic disorder training data correlating biological indices of genetic disorders and genetic markers to genetic disorder labels; and
       training the genetic disorder classifier using the genetic disorder training data;
    inputting the at least one biological index and the at least one genetic marker into the genetic disorder classifier;
    classifying, by the computing device and using the genetic disorder classifier, the at least one biological index and the at least one genetic marker to a positive result for a genetic disorder; and
    generating a sustenance plan as a function of the positive result, wherein generating the sustenance plan further comprises:
       receiving sustenance plan training data;
       training a machine-learning model using the sustenance plan training data, wherein the sustenance plan training data correlates sustenance plans with a historical ameliorative effect on genetic disorders;
       inputting the genetic disorder into the machine-learning model; and
       outputting the sustenance plan as a function of the genetic disorder and the machine-learning model.

11. The method of claim 10, further comprising measuring a progression of the genetic disorder as a function of the at least one biological index.

12. The method of claim 10, further comprising:
    receiving disease training data;
    training a machine-learning model using the disease training data, wherein the disease training data correlates biological indices related to genetic disorders with related disease states; and
    outputting a plurality of related disease states as a function of the machine-learning model.

13. The method of claim 12, further comprising generating the sustenance plan as a function of the plurality of related disease states and the genetic disorder.

14. The method of claim 10, wherein the genetics test data comprises results of a diagnostic genetic testing.

15. The method of claim 10, wherein the genetics test data comprises data from a nutritional assessment.

16. The method of claim 15, wherein the computing device is further configured to output an adverse effect of the nutritional behavior on the genetic disorder as a function of the nutritional assessment.

17. The method of claim 10, wherein generating the sustenance plan further comprises outputting a message independent of a presence of the sustenance plan.

18. The method of claim 10, further comprising:
receiving a second input;
reclassifying the at least one biological index and the at least one genetic marker from the second input to a positive result of the genetic disorder; and
updating the sustenance plan as a function of the second input.

\* \* \* \* \*